US009320213B2

(12) United States Patent
Hendricks

(10) Patent No.: US 9,320,213 B2
(45) Date of Patent: *Apr. 26, 2016

(54) LOW PUNGENCY, LONG DAY ONION

(75) Inventor: Scott Hendricks, Sun Prairie, WI (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 574 days.

This patent is subject to a terminal disclaimer.

(21) Appl. No.: 12/688,406

(22) Filed: Jan. 15, 2010

(65) Prior Publication Data

US 2010/0147717 A1 Jun. 17, 2010

Related U.S. Application Data

(63) Continuation of application No. 12/567,035, filed on Sep. 25, 2009, which is a continuation of application No. 11/486,083, filed on Jul. 14, 2006, now Pat. No. 7,671,255.

(60) Provisional application No. 60/813,625, filed on Jul. 15, 2005.

(51) Int. Cl.
*A01H 5/06* (2006.01)
*A01H 1/00* (2006.01)
*A01H 5/02* (2006.01)
*A23L 1/221* (2006.01)

(52) U.S. Cl.
CPC ............ *A01H 5/0272* (2013.01); *A23L 1/2212* (2013.01)

(58) Field of Classification Search
None
See application file for complete search history.

(56) References Cited

U.S. PATENT DOCUMENTS

| 7,671,255 B2 * | 3/2010 | Hendricks | 800/303 |
| 8,829,303 B1 * | 9/2014 | Colbert et al. | 800/320.1 |
| 2009/0193545 A1 * | 7/2009 | Watson | 800/298 |
| 2010/0011662 A1 * | 1/2010 | Hendricks | 47/1.1 R |

FOREIGN PATENT DOCUMENTS

WO  WO 90/10383  9/1990

OTHER PUBLICATIONS

Havey et al (HortScience (2002) vol. 37; pp. 1086-1087.*
Lancaster et al (Acta Horticulture 555 (2001) pp. 111-115.*
Kopsell et al. Onion cultivars differ in pungency and bulb quality changes during storage. (1997) HortScience; vol. 32; pp. 1260-1263.*
Alan et al (Plant Science (2004) vol. 167; pp. 1055-1066.*
Havel et al. Combining abilities for yield and bulb quality among long and intermediate-day open-pollinated onion populations. (1996) J. Amer. Soc. Hort. Sci.; vol. 121; pp. 604-608.*
Patil et al (HortScience (1995); vol. 30, pp. 765-766.*
Dixondale Farms Web Site—page for Long-Day Onion Varieties (pp. 1-2.*
Resemann et al (Food, Agriculture & Environment (2003) vol. 1; pp. 104-111.*
Havey, M. J. (1998 National Onion Research Conference.*
Mallor et al (Plant Breeding (2011) vol. 130; pp. 55-59.*
Informaciones Tecnicas (2003) Direccion General de Tecnologia Agraria; pp. 1-12.*
Informaciones Tecnicas—Technical Information: "Onion Identification Parameters (II)" (2003) European Agricultural Guidance and Guarantee Fund, Government of Aragon, Dept. of Agriculture; pp. 1-13.*
Bohanec et al. Variations in gynogenic response among long-day onion (Allium cepa L.) accessions. (1999) vol. 18; pp. 737-742.*
Debaene et al. Postharvest flux and genotype X environmental effects for onion-induced antiplatelet activity, punbency, and soluble solids in long-day onion during postharvest cold storage. (1999) J. Amer. Soc. Hort. Sci.; vol. 124; pp. 366-372.*
Simon, P. W. Genetic analysis of pungency and soluble solids in long-storage onions. (1995) Euphytica; vol. 82; pp. 1-8.*
Schwimmer et al. Enzymatic development of pyruvic acid in onion as a measure of pungency. (1961) vol. 9; pp. 301-304.*
Burton, "Enhancing Germplasm with Mass Selection", *Advances in New Crops*, Timber Press, Portland, OR, pp. 99-100 (1990).
Chope et al., "Effect of controlled atmosphere storage on abscisic acid concentration and other biochemical attributes of onion bulbs," *Postharvest Biology and Technology*, 39:233-242 (2006).
Havey et al., "Combining Abilities for Yield and Bulb Quality among Long- and Intermediate-day Open-pollinated Onion Populations," *J. Amer. Soc. Hort. Sci.* 12(4):604-608 (1996).
International Search Report, International Application No. PCT/US06/27647 (International Publication No. WO 2007/011857) (Feb. 29, 2008).
Kopsell et al., "Onion Cultivars Differ in Pungency and Bulb Quality Changes during Storage", *HortScience*, 32(7): 1260-1263 (1997)
Kopsell et al., "Onion Cultivars Differ in Pungency and Bulb Quality Changes during Storage", *HortScience*, 32(7): 1260-1263 (1997).
Schwimmer et al., "Enzymatic Development of Pyruvic Acid in Onion as a Measure of Pungency", *Journal of Agricultural and Food Chemistry*, 9(4):301-304 (1961).
Shock et al., "Pungency of Selected Onion Varieties Before and After Storage", *Oregon State University, Malheur Experiment Station Special Report*, 1055:45-46 (2004).
Shock et al., "Onion Production from Transplants in the Treasure Valley", *Oregon State University, Malheur Experiment Station Special Report*, 1055:47-52 (2004).
Simon, "Genetic Analysis of Pungency and Soluble Solids in Long-Storage Onion," *Euphytica*, 82:1-8 (1995).
Supplementary European Search Report dated Jul. 9, 2009 and issued in EP 06 78 7541.
Hanaoka et al. "Comparison of the Strains in "Sapporo-Ki" Variety of Onion," *Hokkaido Agricultural Experimental Station Bull.*, 74:113-118 (1956).
Abayomi et al., "Implications of spatial and temporal changes in concentration of pyruvate and glucose in onion (*Allium cepa* L.) bulbs during controlled atmosphere storage," *J Sci Food Agric*, 89:683-687 (2009).
Mininger, "United States Onion Production and Marketing," *Acta Hort.*, 555:275-281 (2001).
Randle et al., "Pungency and Sugars of Short-day Onions as Affected by Sulfur Nutrition," *J. Amer. Soc. Hort. Sci.*, 118:(6):766-770 (1993).
Savonen, "Onion bulb formation is strongly linked with day length," *Oregon State University Extension Service*, 1 page. Retrieved on Oct. 18, 2011, from: http://extension.oregonstate.edu/gardening/onion-bulb-formation-strongly-linked-day-length.

(Continued)

*Primary Examiner* — Cathy Kingdon Worley
(74) *Attorney, Agent, or Firm* — Alissa Eagle; Arnold & Porter LLP

(57) ABSTRACT

The present invention includes long-day onion plants comprising bulbs having low pungency and methods for obtaining such onions. The present invention also provides reagents and materials that can be used in the methods for obtaining such onions.

45 Claims, 3 Drawing Sheets

(56) References Cited

OTHER PUBLICATIONS

Sullivan et al., "Nutrient Management for Onions in the Pacific Northwest," *A Pacific Northwest Extension Publication: Oregon State University • Washington State University • University of Idaho*, 28 pages (2001).

Voss et al., "Onion Seed Production in California," *University of California: Division of Agriculture and Natural Resources*, Publications 8008, 10 pages (1999).

"Washington State Malathion Use Summary," Washington State Department of Agriculture/Endangered Species Program, 53 pages (2004).

European Search Report issued on Jan. 20, 2012, in EP Application No. 11186853.5.

Marcos el al., "Pungency evaluation of onion cultivars from the Venezuelan West-Center region by flow injection analysis-UV-visible spectroscopy pyruvate determination," *Talanta*, 64:1299-1303 (2004).

Terry et al., "The Application of Biosensors to Fresh Produce and the Wider Food Industry," *Journal of Agricultural and Food Chemistry*, 53:1309-1316 (2005).

Mikitzel et al., "Flavor and Quality Changes in Sweet Onions during Storage at Room Temperature," *J. Food Quality*, 17:431-445 (1994).

Randle et al., "Streamlining Onion Pungency Analyses," HortScience, 28(1): 60 (1993).

Abayomi et al., "Development of a disposable pyruvate biosensor to determine pungency in onions (*Allium cepa* L.)," Biosensors and Bioelectronics 21: 2176-2179 (2006).

Yasin et al., "Dormancy and sprouting in onion bulbs. II. Changes in sulphur metabolism," Journal of Horticultural Science & Biotechnology 82(1): 97-103 (2007).

Alcala et al., "Comparison of Three Analytical Methods for Measurement of Onion Pungency," Subtropical Plant Science, 50: 41-44 (1998).

Ma et al., "Analysis of methodologies for the study of composition and biochemical carbohydrate changes in harvest and postharvest onion bulbs," International Journal of Experimental Botany, 79: 123-132 (2010).

Jung, <http://www.jungseed.com/dp.asp?pID=04532&c=167>, accessed Nov. 2, 2012.

Dixondale Farms, <http://www.dixondalefarms.com/category/long_day_onions>, accessed Nov. 2, 2012.

Hill, D. E., "Storage and Spanish Onion Trials 1992", The Connecticut Agricultural Experiment Station, New Haven, Connecticut, Bulletin 915, Aug. 1993 (12 pages).

New Rule entitled: "40-7-8-.07 Onion Pungency Analysis", effective Apr. 20, 2010 (9 pages).

Rules and Regulations, Georgia Department of Agriculture: Food Division Regulations: Additional Regulations Applicable to Vidalia Onions, Feb. 20, 2013 (pp. 1-2).

Vegetable and Fruit Improvement Center, "Onion Test Information—Custom Pyruvic Acid Analysis", Feb. 20, 2013 (pp. 1-6).

Miyaura et al., "Seed Productivity of Cytoplasmic Male Sterile Lines of Onion", The Crop Science Society of Japan 29, Report of the Hokkaido Branch (1989).

"New Methods of Breeding F1 Hybrids", *Japanese Journal of Breeding*, 1(1):71 (1951).

Randle et al., "Streamlining Onion Pungency Analyses", *HortScience* 28(1):60 (1993).

Rules and Regulations of the State of Georgia: Georgia Department of Agriculture, Vidalia Onions, Chapter 40-7-8, Oct. 10, 2007 (pp. 1-21).

Yoo et al., "A Simplified Pyruvic Acid Analysis Suitable for Onion Breeding Programs", *HortScience* 30(6):1306 (1995).

Sosai Engei Dai-Jiten (Vegetable Garden Dictionary), p. 252-254 (1997).

\* cited by examiner

FIG. 1A

| Pedigree | Count | | Bulb Wtg | Pungent μmoles/ml |
|---|---|---|---|---|
| Bravo | 26 | Avg | 354.3 | 10.2 |
| | | Stds | 148.9 | 2.4 |
| | | CV | 42.0 | 24.0 |
| Daytona | 17 | Avg | 284.9 | 8.1 |
| | | Stds | 78.0 | 1.2 |
| | | CV | 27.4 | 14.4 |
| Regiment | 29 | Avg | 292.5 | 8.6 |
| | | Stds | 88.1 | 2.1 |
| | | CV | 30.1 | 24.8 |
| Riviera | 28 | Avg | 336.8 | 7.3 |
| | | Stds | 99.3 | 0.8 |
| | | CV | 29.5 | 10.7 |
| Seville | 25 | Avg_ | 339.6 | 8.3 |
| | | Stds | 83.8 | 1.4 |
| | | CV | 24.7 | 16.3 |
| Tamara | 10 | Avg | 380.5 | 10.4 |
| | | Stds | 57.9 | 1.4 |
| | | CV | 15.2 | 13.2 |
| Tesoro | 29 | Avg | 248.1 | 8.5 |
| | | Stds | 41.9 | 2.2 |
| | | CV | 16.9 | 26.0 |
| Teton | 29 | Avg | 271.2 | 9.2 |
| | | Stds | 86.4 | 1.5 |
| | | CV | 31.9 | 16.7 |
| Tribute | 19 | Avg | 210.6 | 8.9 |
| | | Stds | 70.2 | 2.4_ |
| | | CV | 33.3 | 27.0 |
| Valiant | 29 | Avg_ | 266.3 | 8.6 |
| | | Stds | 106.0 | 1.9 |
| | | CV | 39.8 | 22.3 |
| Vantage | 30 | Avg | 264.8 | 7.5 |
| | | Stds | 100.6 | 1.8 |
| | | CV | 38.0 | 24.6 |
| Vaquero | 30 | Avg | 319.1 | 8.1 |
| | | Stds | 108.1 | 1.7 |
| | | CV | 33.9 | 20.5 |
| Vega | 28 | Avg | 325.9 | 9.1 |
| | | Stds | 93.6 | 1.7 |

FIG. 1B

| Pedigree | Count | | Bulb Wtg | Pungent μmoles/ml |
|---|---|---|---|---|
| | | CV | 28.7 | 18.7 |
| Viper | 22 | Avg | 310.5 | 8.1 |
| | | Stds | 87.4 | 2.4 |
| | | CV | 28.1 | 29.6 |
| Vision | 26 | Avg | 280.7 | 6.6 |
| | | Stds | 79.8 | 1.9 |
| | | CV | 28.4 | 28.5 |
| Mira | 28 | Avg | 332.7 | 8.5 |
| | | Stds | 93.0 | 1.6 |
| | | CV | 28.0 | 19.3 |
| Tradewind | 30 | Avg | 257.3 | 8.9 |
| | | Stds | 91.5 | 1.6 |
| | | CV | 35.6 | 17.5 |
| Spinnaker | 29 | Avg | 267.3 | 9.2 |
| | | Stds | 101.5 | 2.0 |
| | | CV | 38.0 | 22.0 |
| Outrigger | 28 | Avg | 266.1 | 7.8 |
| | | Stds | 79.5 | 1.5 |
| | | CV | 29.9 | 19.3 |
| XPH15113 | 26 | Avg | 315.1 | 8.1 |
| | | Stds | 73.3 | 1.5 |
| | | CV | 23.3 | 18.8 |
| King Fisher | 36 | Avg | 286.5 | 8.1 |
| | | Stds | 138.0 | 2.0 |
| | | CV | 48.2 | 24.3 |
| Mariner | 26 | Avg | 254.4 | 8.7 |
| | | Stds | 103.5 | 2.7 |
| | | CV | 40.7 | 31.3 |
| XPH15165 | 27 | Avg | 276.1 | 9.5 |
| | | Stds | 74.7 | 1.9 |
| | | CV | 27.1 | 20.3 |
| XPH15179 | 11 | Avg | 145.6 | 7.4 |
| | | Stds | 27.0 | 0.7 |
| | | CV | 18.5 | 9.7 |
| XPH15221 | 34 | Avg | 266.6 | 7.8 |
| | | Stds | 131.0 | 1.8 |
| | | CV | 49.1 | 23.1 |
| Santa Fe | 27 | Avg | 273.9 | 7.3 |

FIG. 1C

| Pedigree | Count | | Bulb Wtg | Pungent μmole/ml |
|---|---|---|---|---|
| | | Stds | 52.0 | 1.4 |
| | | CV | 19.0 | 18.9 |
| Seahawk | 28 | Avg | 278.0 | 8.8 |
| | | Stds | 103.1 | 1.8 |
| | | CV | 37.1 | 20.1 |
| Red 2 | 30 | Avg | 221.8 | 9.0 |
| | | Stds | 53.5 | 2.4 |
| | | CV | 24.1 | 27.2 |
| XPH15301 | 29 | Avg | 236.2 | 9.6 |
| | | Stds | 73.8 | 1.3 |
| | | CV | 31.3 | 13.7 |
| Super Chef | 20 | Avg | 432.8 | 9.0 |
| | | Stds | 97.5 | 2.4 |
| | | CV | 22.5 | 26.7 |
| XPH77037 | 10 | Avg | 153.7 | 9.3 |
| | | Stds | 16.1 | 2.2 |
| | | CV | 10.4 | 23.9 |
| XPH77043 | 12 | Avg | 181.5 | 6.9 |
| | | Stds | 28.1 | 1.1 |
| | | CV | 15.5 | 16.5 |
| Yula | 26 | Avg | 305.1 | 8.6 |
| | | Stds | 53.8 | 2.4 |
| | | CV | 17.6 | 27.4 |

LOW PUNGENCY, LONG DAY ONION

CROSS-REFERENCE TO RELATED APPLICATIONS

This application is a continuation application of U.S. patent application Ser. No. 12/567,035, filed Sep. 25, 2009, which is a continuation application of U.S. patent application Ser. No. 11/486,083, filed Jul. 14, 2006 (now U.S. Pat. No. 7,671,255), which claims the benefit of U.S. Provisional Application No. 60/813,625, filed Jul. 15, 2005, each of which is herein incorporated by reference.

FIELD OF THE INVENTION

The present invention includes long day onions having low pungency and methods for obtaining such onions. The present invention also provides reagents and materials that can be used in the methods for obtaining such onions.

BACKGROUND

Onions belong to the lily family, Amaryllidaceae, and the genus, *Allium*. Alliums comprise a group of perennial herbs having bulbous, onion-scented underground leaves, including such commonly cultivated crops as garlic, chives, and shallots. It also includes ornamental species grown for their flowers.

Onions are an important vegetable world-wide, ranking second among all vegetables in economic importance with an estimated value of $6 billion dollars annually. The onion is also one of the oldest cultivated vegetables in history. The common garden onions are in the species *Allium cepa*. Onions are classified in numerous ways, by basic use, flavor, color, shape of the bulb, and day length. Onions come in white, yellow, and red colors. The bulb may be rounded, flattened, or torpedo shaped.

Commercial onions include "storage onions", "fresh onions", "pearl or mini onions", and "green onions". "Fresh onions" tend to have a lighter color with a thin skin, a milder, sweeter flavor, and must be eaten fresh as they do not store well. These onions are available in red, yellow, and white colors, and are often sold under the name of their region, e.g., Sweet Imperials, Vidalias, Walla Walla Sweets and Texas Sweets. Perhaps the best known of the fresh onions is the Bermuda onion. Fresh onions are available beginning in March or early April and can be purchased until August.

Storage onions are available from harvest, which is at the beginning of August, and are stored and available throughout the winter months up to about March. Storage onions have a darker skin that is thicker than that of a fresh onion. They are also known for intense, pungent flavor, higher percentage of solids and desirable cooking characteristics. These onions are also available in red, yellow and white colors. Not all long day length type (long day type) onions are suitable for storage. A true storage onion is one that can be harvested in late summer or fall, and stored, under proper conditions, until the spring, when the fresh onion crop is again available.

"Spanish onion", "Spanish onions", or "Spanish type" are terms applied to various long-day onions, generally yellow, though some white, and generally varieties that are large and globe-shaped. Spanish onion is commonly applied to various long day type onions of the type grown in western states of the United States (California, Idaho, Oregon, Washington, Colorado) with a bulb size averaging 300-700 grams (g) (typically over 3 inches up to 4 inches but also up to 5 inches in diameter for bulbs classified as "colossal").

Onion varieties initiate bulbing when both the temperature and a minimum number of daylight hours reach certain levels. When onions are first planted, they initially develop their vegetative growth, with no sign of bulb formation until the proper day length for that onion variety triggers the signal to the plant to stop producing above ground vegetative growth and start forming a bulb. Onions are thus sensitive to the hours of daylight and darkness they receive, and for most varieties it is only when the specific combination of daylight and darkness is reached, that the bulb starts to form. Onions are therefore classified by the degree of day length that will initiate bulb formation. Onions are described as short-, intermediate-, and long-day length types. Short day means that bulbing will initiate at 11 to 12 hours of daylight. Intermediate day is used for onions bulbing at 12 to about 14 hours of daylight. Long day onions require about 14 or more hours of daylight for bulb formation to start.

Growers producing onions in more northerly climates plant long-day length onions. Daylight length varies greatly with latitude, and at higher latitudes long-day onions will produce sufficient top growth before the day length triggers bulbing to produce a large bulb. A short-day onion grown in the North (higher latitudes) will bulb too early and produce relatively small bulbs.

Short day onions are preferred for southern areas such as southern Texas, southern California and Mexico. If a long day type onion is planted in such a short day climate, it may never experience enough day length to trigger the bulbing process.

Onions are also classified on flavor, with the common designations of sweet, mild, and pungent. The flavor of the onion is a result of both the type of onion and the growing conditions. For instance, soils containing a high amount of sulfur result in more pungent flavored onions. Sweetness in onions is caused by the sugars glucose, fructose and sucrose. Onions also contain polymers of fructose called fructans. Onion cultivars differ quite markedly in the relative amounts of sucrose, glucose, fructose and fructans which they contain. They also differ in sugars according to length of storage and location in the bulb. Short day cultivars, which are poor storers, tend to have higher levels of sucrose, fructose and glucose, but hardly any of the fructans. In contrast, long day type cultivars and intermediate storage cultivars such as Pukekohe Longkeeper have less sucrose, glucose and fructose and higher amounts of fructans.

The fructans do not play a role in sweetness. The balance between levels of pungency and levels of sugars determines the perception of pungency in an onion. High levels of pungency can mask high levels of sugars so that the onion is not perceived as sweet. Onions with low levels of pungency but low levels of sugars can be perceived as bland. Ideally a low pungency onion would have high levels of sugars and lower levels of pungency.

It is believed that sunlight strongly influences the development of pungent flavors. While compounds such as sugars and organic acids contribute to the flavor of onions, it is a special class of biologically active organosulfur compounds which give onions their distinctive flavor and aroma. Pungency in onions is caused by these volatile sulfur compounds, some of which affect the eyes when onions are fast cut and induce tearing (often called lachrymatory effect). There are 3 different flavor precursors in onions: 1-propenyl cysteine sulfoxide, which is usually found in the highest concentration; methyl-cysteine sulfoxide, which is normally found in lesser concentration; and propyl cysteine sulfoxide, which is found in the lowest concentration.

Storage conditions may also affect pungency, and though the research is conflicting, most studies show an increase in pungency for most long day type onions during storage. See Shock, C. C., E. B. G. Feibert, and L. D. Saunders. 2004. Pungency of Selected Onion Varieties Before and After Storage. Oregon State University, Malheur Experiment Station Special Report 1055: 45-46.

Within intact cells the enzyme allinase is compartmentalized in the cell vacuole and the flavor precursors are found in the cytoplasm. A reaction, therefore, only occurs when onion tissues are damaged and the enzyme and substrate are brought together as organelles are disrupted. The kinetics of decomposition are different for each specific flavor precursor. The decomposition of 1-propenyl cysteine sulfoxide is almost instantaneous, while the methyl and propyl cysteine sulfoxide decomposition occurs in several minutes. Primary products produced from flavor precursor decomposition include pyruvate, ammonia and chemically unstable sulfenic acids. Among the sulfenic acids is the lachrymator, or tear producing compound, characteristic of onions. The sulfenic acids undergo further rearrangement to form thiosulfinates, which are responsible for the characteristic flavor of onions.

Flavor precursor formation begins with the uptake of sulfate ($SO_4^{-2}$) by the onion, its reduction to sulfide, and subsequent assimilation into cysteine by light-dependent reactions in the leaves of the plant. Glutathione, a tripeptide of cysteine is then synthesized. This is the starting point of the flavor precursor biosynthetic pathway. The pathways leading to the synthesis of each flavor precursor are not fully understood, although sulfur is known to be transformed through several identifiable peptide intermediates, each unique to a specific flavor precursor.

Researchers have recently developed a tool for documenting differences among onion flavor using a laboratory analysis of pyruvic acid development (PAD). Pyruvic acid has been shown to correlate well with consumer flavor perception. The PAD measurements are gaining acceptance within the industry as a clearer index of onion mildness, even though pungency is assessed solely by the amount of enzymatic pyruvic acid. For most commercial onions, pyruvic acid levels fall between about 1 and about 18 micromoles per a gram fresh weight. PAD units are given in micromoles pyruvic acid per gram, fresh weight (μmol/g FW). Short day onions marketed as low pungency onions will typically have PAD values of 5.5 μmol/g FW or less. Onion bulbs having a PAD of 5.5 μmol/g FW or less are considered sweet according to Vidalia Labs sweet onion certification specifications (Shock, C. C., E. B. G. Feibert, and L. D. Saunders. 2004. Onion Production from Transplants in the Treasure Valley. Oregon State University, Malheur Experiment Station Special Report 1055: 4752).

Long day onions are generally grown in the northern states, because of their requirement for long days to initiate bulb production. For this reason, long day type storage varieties do extremely well in the northern states of the United States and Canada, regions that have the required 14-16 hours of daylength during the summer. There are no long day type onions that have low pungency. Some of the commonly planted long day type yellow onion cultivars are Daytona, Ranchero, Granero, Sabroso, Tamara, Hamlet, Fortress, Norstar, Teton, and Vaquero.

Short day varieties do not keep well in storage conditions, and the pungency of short day varieties can climb considerably during storage. Present production in North America and Europe allows harvest of short day onions from mild winter regions from November through April. Long day onions are available fresh in the late summer and as storage onions from September through March, or even year round, have not been available in low pungency varieties. Sweet onions must be imported from the southern hemisphere to fill the gap in sweet onion production (November-February). In the United States, regions like Georgia and Texas produce short day onions from March to June, while low pungency onions available from November to February are short day onions, produced in the southern hemisphere.

There is a need in the art for the development of onions having low pungency, particularly, long-day varieties having low pungency. There is also a need for storage onions in which pungency does not substantially increase during storage.

SUMMARY OF THE INVENTION

In one aspect, the present invention provides a long-day onion plant comprising a bulb having low pungency. In another aspect, the present invention provides a Spanish-type onion plant comprising a bulb having low pungency.

In one aspect, the present invention provides an onion plant requiring about 14 or more, or 14 or more contiguous hours of daylight to initiate bulb formation comprising a bulb having low pungency.

In another aspect, the present invention provides a part of an onion plant requiring about 14 or more, or 14 or more contiguous hours of daylight to initiate bulb formation, where the plant comprises a bulb having a PAD measurement of less than 5.5 μmol/g FW.

In yet a further aspect the present invention provides an onion bulb from a onion plant requiring about 14 or more, or 14 or more contiguous hours of light to initiate bulb formation comprising a bulb having a PAD measurement less than about 5.5 μmol/g FW.

In still another aspect, the present invention provides a container of onion bulbs from onion plants requiring about 14 or more, or 14 or more contiguous hours of light to initiate bulb formation comprising bulbs having an average PAD measurement of less than about 5.5 μmol/g FW.

The present invention also provides a seed of an onion plant requiring about 14 or more, or 14 or more contiguous hours of light to initiate bulb formation, where the seed is capable of producing an onion plant having a bulb comprising a PAD measurement of less than about 5.5 μmol/g FW.

In another aspect, the present invention provides a container of seeds of a onion plant requiring about 14 or more, or 14 or more contiguous hours of light to initiate bulb formation where onion bulbs from greater than 50% of the seeds are low pungency onions, where a population of onion bulbs from the seeds have an average PAD measurement of less than about 5.5 μmol/g FW pyruvate.

The present invention also provides a method of producing a hybrid onion seed comprising crossing a low pungency onion plant requiring about 14 or more or 14 or more hours of light to initiate bulb formation with a second onion plant, and obtaining $F_1$ onion seed.

Also provided herein is a seed of WYL 77-5128B, a sample of said seed having been deposited under NCIMB Accession No. 41329, as well as onion plants grown therefrom and parts thereof.

The present invention also provides a seed of WYL 77-5168B, a sample of said seed having been deposited under NCIMB Accession No. 41330, as well as onion plants grown therefrom and parts thereof.

In yet another aspect, the present invention also provides a hybrid onion plant having a bulb comprising a PAD measurement of less than about 5.5 μmol/g FW, where the onion plant requires about 14 or more, or 14 or more contiguous hours of light to initiate bulb formation.

BRIEF DESCRIPTION OF THE DRAWINGS

Various exemplary aspects of this invention will be described in detail, with reference to the following figures, wherein:

FIGS. 1A-1C present is a chart showing the results of measurements of various pungency and sweetness levels for a number of commercial varieties.

DETAILED DESCRIPTION OF THE PREFERRED ASPECTS

The present invention provides a low pungency, long day type onion plant, onion seeds and onion bulbs (onions) produced by the plant, containers of onion bulbs and containers of onion seeds. In one aspect, the onion produces a white, red or yellow onion bulb. In another aspect, the onion produces Spanish type onions.

Onion plants of the present invention are a variety of *Allium cepa* with improved traits for flavor, in particular, long day onion plants producing long day onion bulbs having low pungency. These and other features and advantages of this invention are described in, or are apparent from, the following detailed description of various exemplary aspects of the devices and methods according to this invention.

"Onion", *Allium cepa* L. (common onion) is a cool season (tolerant of frost) biennial plant. By "biennial plant" it is meant that *Allium cepa* L. produces a bulb in the first season and seeds in the second. Onion plants may be grown at any temperature that allows for the growth and development of the plant. Temperatures that allow for the growth and development of the onion plants of the present invention include those between about 45° F. and about 95° F. or between about 50° F. and about 90° F. Preferable temperatures for growth and development for onion plants of the present invention are between about 55° F. and about 90° F. In another aspect, temperature ranges that allow for seedling growth may be lower than those for plant growth and development. Temperatures that allow for seedling growth include those between about 58° F. and about 87° F. or between about 63° F. and about 82° F. In a preferred aspect, temperatures for seedling growth are those temperatures between about 68° F. to about 77° F.

By "bulb" or "onion bulb" is meant the commercially harvested, edible portion of the onion plant. An onion bulb is comprised of concentric, enlarged fleshy leaf bases, also called scales. Onion bulbs may be developing onion bulbs or mature onion bulbs. In a preferred aspect, the onion bulbs of the present invention are mature onion bulbs.

As used herein, a "mature onion bulb" refers to any onion bulb that is ready for harvest. Generally, when 25-50% of the onion leaf tops have fallen over, the onion is ready for harvest. At maturity, the outer leaf base preferably dries and becomes scaly as the inner leaf bases thicken and develop into a harvestable bulb.

In one aspect, a long day onion plant of the present invention produces an onion bulb that is low pungency. In another aspect, a long day onion plant of the present invention produces an onion bulb having a PAD measurement of less than 5.5 µmol/g FW of pyruvate.

Pungency of onion bulbs may be measured using any method for determining pungency. In one example, pungency is measured by determining the pyruvic acid content of onion bulbs. Pyruvic acid content may be expressed in any units for expressing pyruvic acid content. In a preferred aspect, pyruvic acid content is expressed in micromoles of measured enzymatic pyruvic acid per gram fresh weight of onion flesh (µmol/g FW). In a preferred aspect, measurements are determined using the method for measuring pyruvic acid development (PAD) levels developed by Schwimmer, S.; Weston, W. 1961. Onion Flavor and Odor, Enzymatic Development of Pyruvic Acid in Onions A Measure Of Pungency. Journal Of Agricultural And Food Chemistry 9:301.

In one aspect, low pungency onions of the present invention have PAD measurements of less than 5.5 µmol/g FW of pyruvate. In another aspect, low pungency onions of the present invention have PAD measurements less than 5.0 µmol/g, 4.75 µmol/g, 4.5 µmol/g, 4.25 µmol/g, 4.0 µmol/g, 3.75 µmol/g, or 3.5 µmol/g, FW pyruvate. In another aspect, low pungency onions may have a PAD measurement between about 3.0 µmol/g and about 5.5 µmol/g FW pyruvate, between about 4.0 µmol/g and about 5.5 µmol/g FW pyruvate, between about 4.5 µmol/g and about 5.5 µmol/g FW pyruvate, or between about 5.0 µmol/g and about 5.5 µmol/g FW pyruvate.

In another aspect, low pungency may also be the result of a reduction in organosulfur compounds in an onion bulb compared to a reference long day onion bulb. In one aspect, pungency may be the result of a reduction in organosulfur compounds including 1-propenyl cysteine sulfoxide, methyl-cysteine sulfoxide, or propyl cysteine sulfoxide compared to a reference long day onion. In one aspect, the reference long day onion bulb may be obtained from any commercial long day onion plant. In a preferred aspect, the reference long day onion bulb is a long day onion line, Vision. A reduction in organosulfur compounds may be any reduction in organosulfur compounds. In a preferred aspect, a reduction in organosulfur compounds is a reduction of at least 10%, 15%, 20%, 25%, 30%, 35%, or more of one or more organosulfur compounds compared to a onion bulb from a reference long day onion plant.

In another aspect, pungency may be measured as an average PAD measurement in a population of onion bulbs. A population of onion bulbs may have an average PAD measurement of less than about 5.5 µmol/g, less than 5.0 µmol/g, less than 4.5 µmol/g, less than 4.0 µmol/g, or less than 3.75 µmol/g FW pyruvate. In another aspect, low pungency onions may have an average PAD measurement between about 3.0 µmol/g and about 5.5 µmol/g FW pyruvate, between about 4.0 µmol/g and about 5.5 µmol/g FW pyruvate, between about 4.5 µmol/g and about 5.5 µmol/g FW pyruvate, or between about 5.0 µmol/g and about 5.5 µmol/g FW pyruvate. In one aspect, a population of onion bulbs may be 5, 10, 15, 20, 25, 30, 35, 40, 45, 50, or more onion bulbs.

Average PAD measurements of onion lines, as provided herein, may be determined by averaging the PAD measurements of any number of onion bulbs from an onion plant of the present invention. In one example, average PAD measurements are the average of about 5, 10, 15, 20, 25, 30, 35, 40, 45, or 50 onion bulbs. In a preferred aspect, the onion plant from which the bulb is obtained is a long day onion plant.

An onion attribute such as PAD measurements can be measured at a variety of times. In one aspect, an attribute is measured following growth in a growth chamber. In another aspect, an attribute is measured at the time of harvest. In another aspect, an attribute is measured after storage of the onion bulb at ambient conditions for one day, two days, three days, four days, five days, six days, one week, two weeks, three weeks, four weeks, or five weeks after harvest. In yet another aspect, an attribute is measured after storage of the onion bulb at 5° C. for one day, two days, three days, four days, five days, six days, one week, two weeks, three weeks, one month, two months, three months, four months, five months, or six months after harvest.

Onion plants may be categorized into three categories according to bulb initiation in response to various lengths of daylight. In one aspect, a "short day" length type onion plant (short day, or SD, onion) responds to 11 to 12 hours of daylight for the initiation of bulb formation; an "intermediate day" length type onion plant (intermediate day, or ID, onion) needs 12 to 14 hours of daylight; and a "long day" length type onion plant (long day, or LD onion) requires about 14 or more contiguous hours of daylight for bulb formation to start. In a preferred aspect, long day onion plants require 14 or more contiguous hours of daylight to initiate bulb formation.

Daylight length response periods for bulb initiation for a given type of onion may be expressed in any form, and may be expressed as a number of contiguous hours of daylight for any number of days. In one aspect, the hours of daylight are required for at least one day for the onion plant to initiate bulb formation. In another aspect, an onion plant may require 2, 3, 4, 5, 6, 7, 8, 9, 10, or more days of a given number of contiguous hours of daylight to initiate bulb formation.

Climate and soils may affect pyruvic acid concentrations. Preferably, low pungency onions should be grown on soils which have a naturally low sulphur level. High summer temperatures during the growth period may also increase pyruvic acid concentrations. When producing low pungency onions the use of those sowing and harvesting conditions should be observed that avoid the hottest periods in individual growing regions. Planting density also affects onion pungency. Low plant populations are recommended for low pungency onions. As used herein, then, "similar field conditions" refers to appropriate onion growing conditions for purposes of comparing low pungency lines, i.e., growth in the same field and season, in both a region and under conditions appropriate for producing low pungency onions.

In one aspect, the present invention provides an onion plant requiring about 14 or more, as well as 14 or more contiguous hours of daylight to initiate bulb formation comprising a bulb having low pungency.

In another aspect, the present invention provides seed of an onion plant capable of producing a bulb having a PAD measurement less than about 5.5 µmol/g FW of pyruvate. In a preferred aspect, the onion plant grown from the seed requires about 14 or more, as well as 14 or more contiguous hours of daylight to initiate bulb formation.

The invention also provides long day onions harvested from a low pungency, long day onion, for instance, onions harvested from a plurality of low pungency, long day onion plants grown in a field of onion plants.

The invention further provides a long day onion plant having the trait of producing onion bulbs that are low pungency after storage. In one aspect, the bulbs preferably remain at a low pungency level at least two months of storage, preferably at least about four months under storage, while in further preferred aspects, the onions remain at a low pungency level at least about six months under storage. In one preferred aspect, the PAD measurement after two months storage is less than 5.5 µmol/g FW of pyruvate, though in other preferred aspects, the PAD measurement after two months storage is less than 5.0 µmol/g FW of pyruvate more preferably, less than 4.5 µmol/g FW of pyruvate, even more preferably, less than about 4.0 or 3.75 µmol/g FW of pyruvate.

In another aspect, onion bulbs of the present invention may be stored under any conditions suitable for onion bulb storage without a substantial increase in pungency. In one aspect, storage conditions for long-term storage of onion bulbs from zero to about six months are under controlled climate conditions of about 4 degrees centigrade to about 6 degrees centigrade and relative humidity in the range from about 50% to about 65%. In one aspect, onion bulbs may be stored under such conditions for at least about 1 month, 2 months, 3 months, 4 months, 5 months, or 6 months without a substantial increase in PAD measurement. By "substantial increase" in PAD measurement refers to an increase in PAD measurements by greater than 20% compared to PAD measurements obtained at the time of harvest. In a preferred aspect, the onion bulbs may be stored for such periods without an increase of PAD measurement of more than 15%, 10%, or 5% compared to the PAD measurement at the time of harvest.

In one aspect of the invention, mature onion bulbs harvested from the onion plant have a mean PAD measurement after two months storage that is about equal to or less than the PAD measurement after two months storage for line WYL 77-5128B, when grown under comparable field conditions.

In another aspect of the invention, onions harvested from the onion plant have a mean PAD measurement after two months storage that is about equal to or less than the PAD measurement at harvest for line WYL 77-5168B, when grown under comparable field conditions.

For long-term storage, the onion bulbs may be harvested when fully mature and may be allowed to dry in the sun. The bulbs may be turned, particularly after rainy or damp weather, and damaged material rejected. Containers providing air circulation may be used, including such things as shallow slatted trays and open mesh sacks. In a preferred aspect, exposure to light is avoided, because light can induce sprouting, and the onions are kept dry. In a preferred aspect, an onion bulb can be stored for about 1, 2, 3, 4, 5, 6, 7, or 8 months, with losses of less than 25%.

In another aspect, a low pungency, long day onion is a long day length type onion plant that will produce low pungency mature onion bulbs having a PAD value of less than about 5.5 µmol/g FW, when stored for two months, four months or six months under long-term storage conditions. A low pungency, long day onion will also have a PAD value that is equal to or less, when grown under those comparable field conditions, than the PAD values for onions of the long day length line WYL 77-5168B, under long-term storage conditions for two months, four months or six months. Alternatively, a low pungency, long day onion will have a mean PAD value that is equal to or less, when grown under those comparable field conditions, than the mean PAD values for onions of the long day length line WYL 77-5128B, under long-term storage conditions for two months, four months or six months.

With the present invention, the grower is able to produce a low pungency onion bulbs that can be grown under long day conditions, and which stores well. The trait of bulb production under long day conditions and low pungency line is a great benefit to the grower, as it expands the areas where the desirable low pungency onions may be produced.

Unlike short day onions, the low pungency, long day onions will store for two months or longer periods under long term storage conditions, and hold their low pungency. In one aspect, the long storage capabilities of the low pungency, long day onions, may be used to fill a gap in the present production of low pungency onions (November-February). The low pungency, long day onions may be stored for two months up to six months, or longer, providing a single, continuous source of low pungency onions from growing regions in northern latitudes.

The present invention also provides a container of onion seeds in which bulbs grown from greater than 50% of the seeds are a low pungency, long day type onion plant. In another aspect, bulbs obtained from onion plants grown from greater than 55%, 60%, 65%, 70%, 75%, 80%, 85%, 90%, 95% of the onion seeds in the container are low pungency. In one aspect, a population of bulbs obtained from plants grown from the seeds have an average PAD content of less than 5.5 µmol/g, 5.0 µmol/g, 4.5 µmol/g, 4.0 µmol/g, or 3.75 µmol/g FW of pyruvate. In another aspect, a population of bulbs obtained from onion plants grown from the seeds have an average PAD measurement between about 3.75 µmol/g and about 5.5 µmol/g FW pyruvate, between about 4.0 µmol/g and about 5.5 µmol/g FW of pyruvate, between about 4.5 µmol/g and about 5.5 µmol/g FW of pyruvate, or between about 5.0 µmol/g and about 5.5 µmol/g FW of pyruvate. A population of onion bulbs may contain at least about 10, 15, 20, 25, 30, 35, 40, 45, 50, 100, 200, 500, or 1000 or more onion bulbs.

The container of onion seeds may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10, ounces, 1 pound, 2 pounds, 3 pounds, 4 pounds, 5 pounds or more seeds.

Containers of onion seeds may be any container available in the art. By way of non-limiting example, a container may be a box, a bag, a packet, a pouch, a tape roll, or a tube.

In another aspect, the present invention also provides a container of onion bulbs in which greater than 50% of the bulbs are a low pungency from a long day type onion plant. In another aspect, greater than 55%, 60%, 65%, 70%, 75%, 80%, 85%, 90%, 95% of the onion bulbs in the container are low pungency. In one aspect, a population of bulbs in the container have an average PAD content of less than 5.5 µmol/g, 5.0 µmol/g, 4.5 µmol/g, 4.0 µmol/g, or 3.75 µmol/g FW of pyruvate. In another aspect, a population of bulbs have an average PAD measurement between about 3.75 µmol/g and about 5.5 µmol/g FW pyruvate, between about 4.0 µmol/g and about 5.5 µmol/g FW of pyruvate, between about 4.5 µmol/g and about 5.5 µmol/g FW of pyruvate, or between about 5.0 µmol/g and about 5.5 µmol/g FW of pyruvate. A population of onion bulbs may contain at least about 5, 10, 15, 20, 25, 30, 35, 40, 45, 50, 100, 200, 500, or 1000 or more onion bulbs.

The container of onion bulbs may contain any number, weight or volume of bulbs. For example, a container can contain at least, or greater than, about 5, 10, 15, 20, 25, 30, 35, 40, 45, 50, or 100 bulbs. Alternatively, the container can contain at least, or greater than, about 1 pound, 2 pounds, 3 pounds, 4 pounds, 5 pounds or more of bulbs.

Containers of onion bulbs may be any container available in the art. By way of non-limiting example, a container may be a box, a flat, a bag, a packet, or a bunch. A container of onion bulbs of the present invention may be found in any location, including, but not limited to a warehouse, a distributor, a wholesaler, or a retail market, such as a grocery store.

The invention further provides a method of producing an onion crop comprising growing a plurality of low pungency, long day onion plants and harvesting long day onions from the onion plants. Long day onions harvested according to this method are also provided.

In one aspect, onion plants of the present invention may be maintained as open pollinated lines, half-sib lines, or male sterile lines, and may vary phenotypically with regard to such traits as size, shape, and color. In another aspect, the present invention provides inbred onion lines requiring 14 or more hours of contiguous daylight to initiate bulb formation, having low pungency. Male sterile inbreds may be used in the production of onion hybrids of the present invention. The development of onion hybrids in a onion plant breeding program may involve the development of homozygous inbred lines, the crossing of these lines, and the evaluation of the crosses. In another aspect of the present invention, onion plant breeding programs may combine the genetic backgrounds from two or more inbred lines or various other germplasm sources into breeding populations from which new inbred lines may be developed by self or sib pollinating and selection of desired phenotypes. Plant breeding techniques known in the art and used in an onion plant breeding program include, but are not limited to, recurrent selection, backcrossing, double haploids, pedigree breeding, restriction fragment length polymorphism enhanced selection, genetic marker enhanced selection, and transformation. In one aspect, a combination of these techniques may be used. Thus, inbred lines derived from onion plants of the present invention may be developed using plant breeding techniques as described herein. New inbred onion lines may be crossed with other inbred lines and the hybrids from these crosses may be evaluated to determine which of those have commercial potential.

Backcrossing methods can be used with the onion plants of the present invention to improve or introduce a particular characteristic or set of characteristics into an inbred. The term "backcrossing" as used herein refers to the repeated crossing of a hybrid progeny back to one of the parental onion plants for that inbred. The parental onion plant which contributes the gene for the desired characteristic is termed the nonrecurrent, or donor, parent. This terminology refers to the fact that the nonrecurrent parent is used one time in the backcross protocol and therefore does not recur. The parental onion plant to which the gene or genes from the nonrecurrent parent are transferred is known as the recurrent parent, as it is used for several rounds in the backcrossing protocol. In a typical backcross protocol, the original inbred of interest (recurrent parent) is crossed to a second inbred (nonrecurrent parent) that carries the trait or traits of interest to be transferred. The resulting progeny from this cross are then crossed again to the recurrent parent and the process is repeated until an onion plant is obtained wherein essentially all of the desired morphological and physiological characteristics of the recurrent parent are recovered in the converted plant, in addition to the one or few transferred traits of the nonrecurrent parent. Typically, four or more backcross generations may be required, with selection for the desired trait, before the progeny will contain essentially all genes of the recurrent parent except for the genes controlling the desired trait(s). Where molecular markers are available for use during the selection process, the program may be accelerated. The last backcross generation is then selfed to give pure breeding progeny for the gene(s) being transferred.

When the term "inbred", "inbred plant" or "inbred onion" is used in the context of the present invention, this also includes any single gene conversions of that inbred. The term single gene converted plant as used herein refers to those onion plants which are developed by a plant breeding technique called backcrossing wherein essentially all of the desired morphological and physiological characteristics of an inbred are recovered in addition to the single gene transferred into the inbred via the backcrossing technique.

Any onion plant can be used in conjunction with the onion plants disclosed herein. In a preferred aspect, the source of low pungency is an elite plant. In an aspect, low pungency onions may be produced by breeding with the following long day sources: Daytona, Ranchero, Granero, Sabroso, Tamara, Hamlet, Fortress, Norstar, Teton, and Vaquero. FIG. 1 provides a chart of measurements of various pungency and sweetness parameters for a number of commercially available (and a few developmental) long day length onion varieties. As will be apparent, a typical long day type onion coming out of storage during the winter months will have a PAD in the 6.2-12 µmol/g FW range, and will be quite pungent. In an aspect, a low pungency onion plant of the present invention may be crossed with any inbred onion line having desired properties.

As used herein, an "elite line" is any line that has resulted from breeding and selection for superior agronomic performance. An elite plant is any plant from an elite line. Plants can be chosen from Spanish onion or other long day germplasm and can be screened for low PAD values.

Onion plants of the present invention may have been self-pollinated and selected for type over many generations to become homozygous at almost all gene loci and produce a uniform population of true breeding progeny. A cross between two such plants produces a uniform population of hybrid plants that are heterozygous for many gene loci. The development of inbred plants generally requires at least about 2 generations of selfing followed by mass selection or sib crossing. Inbred plants may then be cross-bred in an attempt to develop improved $F_1$ hybrids. Hybrids are then screened and evaluated in small scale field trials. Typically, about 10 to 15 phenotypic traits, selected for their potential commercial value, are measured.

The present invention also provides progeny of low pungency onions having sufficient genetic material to retain the traits of the onion plants of the present invention. As used herein, the progeny include not only, without limitation, the products of any cross (be it a backcross or otherwise) between two plants, but all progeny whose pedigree traces back to the original cross. In one aspect, without limitation, such progeny include plants that have 50%, 25%, 12.5% or less genetic material derived from one of the two originally crossed plants. As used herein, a second plant is derived from a first plant if the second plant's pedigree includes the first plant.

Plants generated using a method of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using any method available, such as, marker assisted selection of the progeny of any cross. It is further understood that any commercial and non-commercial cultivars can be utilized in a breeding program. Factors such as, for example, emergence vigor, vegetative vigor, stress tolerance, disease resistance, flowering, seed set, seed size, seed density, standability, and bulb size will generally dictate the choice.

The present invention provides processes of preparing novel onion plants and onion plants produced by such processes. In accordance with such a process, a first parent onion plant may be crossed with a second parent onion plant wherein at least one of the first and second onion plants is an inbred low pungency, long day onion plant as described herein. One application of the process is in the production of $F_1$ hybrid plants. Another important aspect of this process is that it can be used for the development of novel inbred lines. For example, an inbred low pungency onion plant as described herein could be crossed to any second plant, and the resulting hybrid progeny each selfed or sib-pollinated for about 2 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified.

Onion plants of the present invention can be crossed by either natural techniques, such as through insect pollination. In one aspect, crossing comprises the steps of:

(a) planting in pollinating proximity seeds or bulbs of a first and a second parent onion plant, and preferably, seeds or bulbs of a first inbred onion plant and a second, distinct inbred onion plant;

(b) cultivating or growing the seeds or bulbs of the first and second parent onion plants into plants that bear flowers;

(c) allowing natural cross-pollination to occur between the first and second parent onion plants;

(d) harvesting seeds produced on the parent onion plants; and, where desired, (e) growing the harvested seed into a onion plant, preferably, a hybrid onion plant.

Parental plants may be planted in pollinating proximity to each other by planting the parental plants in alternating rows, in blocks, in breeding cages or in any other convenient planting pattern. Where the parental plants differ in timing of sexual maturity, it may be desired to plant the slower maturing plant first, thereby ensuring the availability of pollen from the male parent during the time at which the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

Alternatively, in another aspect of the invention, both first and second parent onion plants can be a low pungency, long day onion plant as described herein. Thus, any onion plant produced using a low pungency, long day onion plant as described herein forms a part of the invention. As used herein, crossing can mean selfing, sib-crossing, backcrossing, crossing to another or the same inbred, crossing to populations, and the like. All onion plants produced using a low pungency, long day onion plant as described herein as a parent are, therefore, within the scope of this invention.

A further aspect of the present invention relates to tissue cultures of the onion plants described herein. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryo, leaf, peduncle, pedicel, anther, meristem, bulb, stump and stem, explants, and the like. In a preferred aspect, the tissue culture comprises embryos, protoplasts, meristematic cells, pollen, leaves or anthers derived from immature tissues of these plant parts. Means for preparing and maintaining plant tissue cultures are well known in the art.

Seed of the inbred long day onion (*Allium cepa*) plants designated WYL 77-5128B have been deposited at the National Collections of Industrial and Marine Bacteria (NCIMB Limited, Ferguson Building, Craibstone Estate, Bucksburn, Aberdeen, Scotland; AB21 9YA, UK) as accession No. 41329. Seed of the inbred long day onion plants designated WYL 77-5168B have similarly been deposited at NCIMB, as accession No. 41330. The seed, plants grown from the seed, and seed derived from such plants, are also provided herein.

In a further aspect of the invention, seed is provided for a long day onion plant having as at least one parent a plant grown from seed of any one of long day onion plants WYL 77-5128B and WYL 77-5168B. The plant may be a hybrid plant having one or both parents selected from the long day onion plants WYL 77-5128B and WYL 77-5168B. The invention further provides a long day onion plant, or parts thereof, produced by growing seed of such a long day onion plant.

The invention also provides long day onions harvested from a long day onion plant grown from the long day onion plant produced from such seed or by any means of asexual reproduction.

The invention also provides long day onion plants having the physiological and morphological characteristics of the long day onion plants WYL 77-5128B and WYL 77-5168B. The invention contemplates plants or plant products produced from protoplasts or regenerable cells from the long day onion plants, using tissue culture where the cells or protoplasts are produced from a plant tissue selected from the group consisting of leaf, pollen, cotyledon, hypocotyl, embryos, root, pod, flower, shoot and stem.

Another aspect of the invention provides low pungency, long day onion plants or parts thereof, where the plant or parts thereof have been transformed to contain one or more transgenes operably linked to regulatory elements functional in the long day onion plant.

A still further aspect of the invention provides pollen or an ovule of WYL 77-5128B and WYL 77-5168B, or an onion tissue culture derived from cells of such long day onion plants, particularly a long day onion plant regenerated from such tissue culture and having the trait of being low pungency, long day length.

Use of onion plants or any parts thereof of the invention, such as for breeding purposes, is also provided by the invention. More particularly, a method is contemplated whereby an $F_1$ onion plant is grown from $F_1$ seed resulting from a cross of a long day, low pungency onion plant of the invention as at least one parent onion plant, and selecting progeny onion plants having desired traits. In a further preferred aspect, two or more generations of back crossing to one of the parent onion plants is used in breeding a new line of long day, low pungency onion plant.

WYL 77-5168B is a long day Spanish onion breeding line, combining all the desired features of typical long day Spanish onions with the additional feature of low pungency. The variety that most closely resembles is WYL 77-5168B is Vision. The comparative characteristic that most readily distinguishes the low pungency varieties such as WYL77-5128B from all other long day varieties is the unique low pungency ("mildness") of WYL 77-5168B. This level of low pungency is unique for onions that respond to photoperiod under long day conditions to induce bulbing.

Seed from *Allium cepa* breeding line WYL 77-5168B, described above, was deposited on 24 Jun. 2005 with NCIMB Ltd., as Accession No. NCIMB 41330 *Allium cepa* WYL 77-5168B.

WYL 77-5128B is long day Spanish onion breeding line, combining all the desired features of typical long day Spanish onions with the additional feature of low pungency. Again, the variety that most closely resembles WYL 77-5128B is Vision. WYL 77-5128B produces a low pungency onion under photoperiods of long day conditions to induce bulbing. Seed from *Allium cepa* breeding line WYL 77-5128B, described above, was deposited on 24 Jun. 2005 with NCIMB Ltd., as Accession No. NCIMB 41329 *Allium cepa* WYL 77-5128B.

In a preferred aspect, the long day, low pungency onion plants of the present invention may be used in the production of hybrid seed. Any time a low pungency onion plant as described herein is crossed with another, different, onion inbred, a first generation ($F_1$) onion hybrid plant is produced.

As such, an $F_1$ hybrid onion plant can be produced by crossing a low pungency onion plant, for example, as described herein with any second inbred onion plant. Essentially any other onion plant can be used to produce a hybrid onion plant having a long day, low pungency onion plant as described herein as one parent. All that is required is that the second plant be fertile, which onion plants naturally are.

Onion has a diploid phase which means two conditions of a gene (two alleles) occupy each locus (position on a chromosome). If the alleles are the same at a locus, there is said to be homozygosity. If they are different, there is said to be heterozygosity. Because many loci when homozygous are deleterious to the plant, in particular leading to reduced vigor, poor bulb quality, weak and/or poor growth, production of inbred plants is an unpredictable and arduous process. Under some conditions, heterozygous advantage at some loci effectively bars perpetuation of homozygosity.

A single cross hybrid onion variety is the cross of two inbred plants, each of which has a genotype which complements the genotype of the other. Typically, $F_1$ hybrids are more vigorous than their inbred parents. This hybrid vigor, or heterosis, is manifested in many polygenic traits, including markedly improved yields, better roots, better uniformity and better insect and disease resistance. In the development of hybrids only the $F_1$ hybrid plants are typically sought. An $F_1$ single cross hybrid is produced when two inbred plants are crossed. A three way cross hybrid is produced from three inbred plants crossed initially between two inbreds (A×B) and then crossing the $F_1$ hybrid with a third inbred line (A×B)×C.

Any of the onion varieties known to those of skill in the art can be crossed with a long day, low pungency onion line of the present invention to produce a hybrid plant.

When an inbred low pungency onion plant as described herein is crossed with another inbred plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Therefore, a decision to use one parent plant as a male or female may be made based on any such characteristics as is well known to those of skill in the art.

The development of new varieties using one or more starting varieties is well known in the art. In accordance with the invention, novel varieties may be created by crossing an inbred long day, low pungency onion plant as described herein followed by multiple generations of breeding according to such well known methods. New varieties may be created by crossing a long day, low pungency onion plant as described herein with any second plant. In selecting such a second plant to cross for the purpose of developing novel inbred lines, it may be desired to choose those plants which either themselves exhibit one or more selected desirable characteristics or which exhibit the desired characteristic(s) when in hybrid combination. Examples of potentially desired characteristics include greater yield, resistance to insecticides, herbicides, pests, and disease, tolerance to heat and drought, reduced time to crop maturity, better agronomic quality, higher nutritional value, and uniformity in germination times, growth rate, maturity, and bulb size.

Once initial crosses have been made with a long day, low pungency onion plant of the present invention, inbreeding takes place to produce new inbred varieties. Inbreeding requires manipulation by human breeders. Even in the extremely unlikely event inbreeding rather than crossbreeding occurred in natural onion, achievement of complete inbreeding cannot be expected in nature due to well known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed or sib-crossed and selected in successive generations. Each succeeding generation becomes more homogeneous as a result of self-pollination and selection. Typically, this method of breeding involves one or two generations of selfing or sib-crossing followed by mass selection or sibbing: $S_1 \rightarrow S_2$; $S_2 \rightarrow S_3$. After at least five generations, the inbred plant is considered genetically pure. The onion plants of the present invention may be genetically pure or $S_1$, $S_2$, $S_3$, etc.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, herbicide resistance, resistance for bacterial, fungal, or viral disease, insect resistance, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Many useful traits are those which are introduced by genetic transformation techniques. Methods for the genetic transformation of onion are known to those of skill in the art. For example, methods which have been described for the genetic transformation of onion may include electroporation, electrotransformation, microprojectile bombardment, *Agrobacterium*-mediated transformation, direct DNA uptake transformation of protoplasts and silicon carbide fiber-mediated transformation. See, e.g., Khachatourians, G., et al., eds., Transgenic Plants and Crops, Marcel Dekker, Inc. (2002).

It is understood to those of skill in the art that a transgene need not be directly transformed into a plant, as techniques for the production of stably transformed onion plants that pass single loci to progeny by Mendelian inheritance is well known in the art. Such loci may therefore be passed from parent plant to progeny plants by standard plant breeding techniques that are well known in the art. Examples of traits that may be introduced into an onion plant according to the invention include, for example, male sterility, herbicide resistance, disease resistance, insect resistance, and enhanced nutritional quality.

PCR and Southern hybridization are two examples of molecular techniques that can be used for confirmation of the presence of a given locus and thus conversion of that locus.

Every reference, patent, or other published work cited above is herein incorporated by reference in its entirety.

EXAMPLES

WYL 77-5128B and WYL 77-5168B are long day onions producing bulbs under long day conditions. Various field trials were conducted with breeding lines in selecting low pungency, long day onions, comparing the low pungency, long day onions with control long day onions, including Vision, grown under comparable field conditions. Vision is a CMS hybrid presently marketed by *Seminis*, a hybrid yellow Spanish type onion of long day class, with full season maturity and excellent storage.

Collected onion samples were analyzed for pyruvate (PAD levels), according to the methods described (Schwimmer, S.; Weston, W. 1961. Onion Flavor and Odor, Enzymatic Development of Pyruvic Acid in Onions A Measure Of Pungency. Journal Of Agricultural And Food Chemistry 9:301).

As is true with other onion cultivars, a small percentage of variants can occur within commercially acceptable limits for almost any characteristics during the course of onion multiplication. No variants were observed during the years in which WYL 77-5128B and WYL 77-5168B were observed to be uniform and stable.

Example 1

WYL 77-5168B Long Day Onion

WYL 77-5168B, a long day onion inbred, was developed by mass selection from a synthetic gene pool of Yellow Sweet Spanish onion (synthetic gene pool YSS-715B). Mass selection is the formation of a composite population through selective harvest of individuals among a heterozygous population. See, Burton, G. W. 1990. Enhancing germplasm with mass selection. p. 99-100. In: J. Janick and J. E. Simon (eds.), Advances in new crops. Timber Press, Portland, Oreg.

Synthetic gene pool YSS-715B was developed from a pool of YSS 53-351 B (50%), and YSS 805 (50%). This pool was created for other phenotypic purposes, with no initial interest with regard to pungency.

WYL 77-5168B is a Spanish onion line that is large in size, with a round bulb shape and medium colored skin. Tops are medium and somewhat floppy. Storage length of WYL 77-5168B is medium term. Maturity of WYL 77-5168B is full-season for a Spanish type onion.

Year 1 Mass 1 generation bulbs were selected from synthetic YSS-715B.

Year 2 Seed was produced on the M1 bulb selection.

Year 3 Mass 2 generation bulbs were selected from 1995 seed production.

Year 4 Seed was produced in cage 97-575 from the 1996 M2 bulb selection.

Year 5 Mass 3 generation bulbs were selected from source 97-575.

Year 6 Seed was produced from M3 bulb selections in cage 99-327-1. Additional bulbs were also grown of source 97-575 in row number 99-7099 and bulb selections were made.

Year 7 Mass 4 generation seed was produced in cage 00333-1 from bulbs grown in row number 99-7099.

Year 8 Bulbs were grown in row 01OS3164 from original seed source 00333-1 and parent breeding line WYL 77-5168B was assigned. WYL 77-5168B showed good characteristics for size, skin retention and lack of bolters (seed-stem formation, or "bolting", produces poor quality bulbs with a hard center making them unmarketable). This line also produced sufficient seed for further development. In the initial screen, WYL 77-5168B had a mean PAD of 4.53 µmol/g FW. WYL 77-5128B had a mean PAD of 6.48 µmol/g FW. Three other lines, less favorable for other traits, had mean PADs of 5.82, 6.16 and 6.22 µmol/g FW. Of the remaining lines tested, there were ten between 6.5 and 7.0, twenty-one between 7.0 and 7.5, eleven between 7.5 and 8.0, fourteen between 8.0 and 8.5, fourteen between 8.5 and 9.0, ten between 9.0 and 9.5, three between 9.5 and 10.0, eight between 10.0 and 10.5, and five greater than 10.5. The low PADS for certain of the lines led to selection for those lines in subsequent generations based on mean PAD levels after two months storage under long term storage conditions.

Year 9 Mass 5 generation seed was produced in cage RNG4005 from bulbs grown in row number 01OS3164. Additional bulbs were grown in row 02053097 from seed source 00333-1. Pungency testing on these bulbs showed line WYL 77-5168B having pungency level of 4.53 µmol/g FW PAD (min 2.14, max 6.98) after two months of storage.

Year 10 Seed Production Cycle—Mass 5 generation seed was produced in cages RNR5613, RNR5616, RNR5617, RNR5619 from bulbs grown in row number 02053097 from original source 00333-1 (M-4). Pungency testing on these bulbs showed line WYL 77-5168B having a pungency level of 4.51 PAD (min 2.30, max 9.97) after six months of storage. Cage RNR5619 was a low pungency selection with a mean of 3.91 PAD (min 2.56, max 4.96).

Year 10 Bulb Production Cycle—Bulbs of WYL 77-5168B were grown in bulb row 03054045 from original seed source 00333-1. Pungency testing on bulb row 03054045 showed line WYL 77-5168B having a mean pungency of 5.16 PAD (thin 1.82, max 11.94) after six months of storage. Vision was grown in rows 03OS 1283 and 03OS 1317 and pooled for analysis and had a mean pungency level of 9.15 PAD (min 6.25, max 15.44) after six months of storage.

Year 11 Seed Production Cycle—Seed was produced of line WYL 77-5168B in cage RNV4012 from original seed source 00333-1. RNV4012 was a low pungency selection with-a mean level of 3.74 PAD (min 1.82, max 4.57).

Year 11 Bulb Production Cycle—The bulbs of WYL 77-5168B from an original source 00333-01 were tested after two months of storage and showed a mean pungency level of 6.02 PAD (min 4.28, max 8.19). An advanced selection of WYL 77-5168B, RNR5616-2 was grown in row 04OS7076 showed a mean pungency level of 4.09 PAD (min 3.52, max 5.75) after two months of storage. An advanced selection of WYL 77-5168B, RNR5616-12 was grown in row 04OS7085 showed a mean pungency level of 4.87 PAD (min 3.80, max 7.45) after two months of storage. An advanced selection of WYL 77-5168B, RNR5616-7 was grown in row 04OS57081 showed a mean pungency level of 5.09 PAD (min 3.68, max 6.75) after two months of storage. An advanced selection of WYL 77-5168B grown in row 04OS7086, RNR5616-15 showed a mean pungency level of 5.15 PAD (min 3.86, max 6.08) after two months of storage.

An advanced selection of WYL 77-5168B, RNR5616-3 was grown in row 04OS7077 showed a mean pungency level of 5.30 PAD (min 3.70, max 5.75) after two months of storage. Vision was also analyzed and from replication 1 showed a mean pungency level of 6.07 PAD (min 4.94, max 7.24) and from replication 2 showed a mean pungency level of 6.25 (min 5.14, max 7.40). Peruvian Sweets (Bland Farms source), short day type (SD) onions imported and purchased for this study, showed a mean pyruvate level of 6.04 PAD (min 4.67, max 7.94).

Selection criteria in the field represent a balance of characteristics related to productivity and fit to the market including, yield potential, foliage, bulb shape, bulb skin, bolting tolerance, long storage, and resistance to pink root and *fusarium*.

Observations in Year 8, Year 9, Year 10, and Year 11 confirm that breeding line WYL 77-5168B is uniform and stable within commercially acceptable limits.

Example 2

WYL 77-5128B. Long, Day Onion

WYL 77-5128B, a long day Spanish onion inbred, was developed by mass selection from a synthetic gene pool of Yellow Sweet Spanish (synthetic gene pool YSS-FR713B).

Synthetic gene pool YSS-FR713B was developed from a pool of YSS-Giano (50%), YSS 53-351B (25%), and YSS Peckham (25%).

WYL 77-5128B is a low pungency Spanish onion line, that is medium in size, with a high globe shape and dark colored skin. Tops are large and upright. Storage length of WYL 77-5128B is long term. Maturity of WYL 77-5128B is mid season for a Spanish type onion Year 1 Mass 1 generation bulbs were selected from synthetic YSS-FR713B.

Year 2 Seed was produced on the M1 bulb selection.

Year 3 Mass 2 generation bulbs were selected from 1996 seed production.

Year 4 Seed was produced in cage 97-547 from the 1996 M2 bulb selection.

Year 5 Mass 3 generation bulbs were selected from source 97-547.

Year 6 Seed was produced from M3 bulb selections in cage 00335-1.

Year 7 Mass 4 generation bulbs were selected in row O1OS3182 (from original seed source 00335-1) and parent breeding line WYL 77-5128B was assigned. As noted above, selections from this point forward were screened for mean PAD levels after two months storage under long term storage conditions.

Year 8 Seed was produced from 01OS3182 bulb production in cages RNG3243 and RNG3968 (M4 seed). Bulbs were grown in row 02OS3029 from original seed source 00335-1

Pungency testing on these bulbs showed line WYL 77-5128B having pungency level of 5.40 PAD (min 3.41, max 8.23) after two months of storage.

Year 9 Seed production of Mass 4 generation seed was produced in cage RNR5724 and RNR5621 from bulbs grown in row number 02OS3029. Cage RNR5621 was a low pungency selection with a mean of 4.72 (min 3.41, max 5.58).

Year 9 Bulb production Cycle—Bulbs were grown in row 03OS4043 from seed source 00335-1. Pungency testing on bulb row 03OS4043 showed line WYL77-5128B having a mean pungency of 7.87 PAD (min 4.38, max 11.93) after six months of storage. Vision was grown in rows 03OS1283 and 03OS1317 and pooled for analysis and had a mean pungency level of 9.15 PAD (min 6.25, max 15.44) after six months of storage. This trial received hail damage and did not develop normal size, resulting in smaller more pungent bulbs.

Year 10 Seed was produced of line WYL 77-5128B in cage RNV4014 from seed source 00335-1. RNV4014 was a low pungency selection with a mean level of 5.96 PAD (min 4.38, max 6.50).

Year 10 Bulb production cycle—The bulbs of selection WYL 77-5128B from original seed source 00335-1 were tested after two months of storage and showed a mean pungency level of 5.32 PAD (min 3.24, max 6.95). An advanced selection of WYL 77-5128B, RNR5621-13 was grown in row 04OS7097 showed a mean pungency level of 4.29 PAD (min 3.12, max 5.60) after two months of storage. An advanced selection of WYL 77-5128B, RNR5621-15 was grown in row 04OS7099 showed a mean pungency level of 4.37 PAD (min 3.40, max 5.59) after two months of storage. An advanced selection of WYL 77-5128B, RNR5621-5 was grown in row 04OS7090 showed a mean pungency level of 4.53 PAD (min 3.32, max 6.20) after two months of storage. An advanced selection of WYL 77-5128B, RNR5621-8 was grown in row 04OS7093 showed a mean pungency level of 4.67 PAD (min 3.26, max 5.60) after two months of storage. An advanced selection of WYL 77-5128B, RNR5621-12 was grown in row 04OS7096 showed a mean pungency level of 4.81 PAD (min 3.88, max 6.49) after two months of storage. An advanced selection of WYL 77-5128B, RNR5621-10 was grown in row 04OS7095 showed a mean pungency level of 4.87 PAD (min 3.94, max 5.75) after two months of storage. An advanced selection of WYL 77-5128B, RNR5621-3 was grown in row 04OS7089 showed a mean pungency level of 5.03 PAD (min 3.82, max 6.01) after two months of storage. An advanced selection of WYL 77-5128B, RNR5621 was grown in row 04OS7009 showed a mean pungency level of 5.10 PAD (min 3.65, max 8.79) after two months of storage. Vision was also analyzed and from replication 1 showed a mean pungency level of 6.07 PAD (min 4.94, max 7.24) and from replication 2 showed a mean pungency level of 6.25 (min 5.14, max 7.40). Peruvian Sweets (Bland Farms source), SD onions imported and purchased for this study, showed a mean pyruvate level of 6.04 PAD (min 4.67, max 7.94).

Selection criteria in the field represent a balance of characteristics related to productivity and fit to the market including, yield potential, foliage, bulb shape, bulb skin, bolting tolerance, long storage, and resistance to pink root and *fusarium*.

Example 3

Pungency in Storage

Harvested low pungency long day onions were stored under storage conditions of 5 degrees centigrade and 50% relative humidity for 6 months.

Tables 1 and 2 below provide raw data for mean PAD measurements after two and six months storage under long term storage conditions on the lines noted above.

TABLE 1

History of pungency selection of line WYL 77-5168B
Mean PAD

| Source | Year 9 Bulb Harvest | Year 10 Bulb Harvest | Year 11 Bulb Harvest | Year 12 Bulb Harvest |
| --- | --- | --- | --- | --- |
| 00333-1 (original source) | 4.53 g FW (2) | 4.51 g FW (2)(3) | 6.02 g FW (1) 4.20 g FW (2) | 4.70 g FW (1) 3.90 g FW (2) |
| RNR5619 (selection of 00333-1) | | | 5.60 g FW (1) 4.16 g FW (2) | |
| RNR5616-2 (selection of 00333-1) | | | 4.09 g FW (1) 4.98 g FW (2) | |
| RNR5616-3 (selection of 00333-1) | | | 5.30 g FW (1) 4.24 g FW (2) | |
| RNR 5616-7 (selection of 00333-1) | | | 5.09 g FW (1) 4.12 g FW (2) | |
| RNR 5616-12 (selection of 00333-1) | | | 4.87 g FW (1) 4.91 g FW (2) | |
| RNR 5616-15 (selection of 00333-1) | | | 5.15 g FW (1) 3.28 g FW (2) | |
| Vidalia Sweets (SD) | | 9.15 g FW (4) | 3.34 g FW (4) | 3.20 g FW (4) |
| Vision (long day Spanish Variety) | | 9.15 g FW (3) | 6.16 g FW (1) 8.71 g FW (2) | 5.50 g FW (1) 7.35 g FW (2) |
| TX 1015Y (SD control variety) | | | 4.69 g FW (4) | |
| Peruvian Sweet (SD) | | | 6.02 g FW (4) | 4.3 g FW (4) |

(1) After two months storage
(2) After six months storage
(3) Field received damage from a hail storm prior to harvest, which reduced size and stopped normal maturity.
(4) Locally purchased source

TABLE 2

History of pungency selection of line WYL 77-5128B
Mean PAD

| Source Bulb Harvest | Year 8 Bulb Harvest | Year 9 Bulb Harvest | Year 10 Bulb Harvest | Year 11 Bulb Harvest |
| --- | --- | --- | --- | --- |
| 00335-1 (original source) | 5.40 g FW (2) | 7.87 g FW (2)(3) | 5.32 g FW (1) 6.30 g FW (2) | 4.70 g FW (1) 6.40 g FW (2) |
| RNR 5621 (selection of 00335-1) | | | 5.10 g FW (1) 6.21 g FW (2) | |
| RNR 5621-3 (selection of 00335-1) | | | 5.06 g FW (1) 5.84 g FW (2) | |
| RNR 5621-5 (selection of 00335-1) | | | 4.53 g FW (1) 6.35 g FW (2) | |

TABLE 2-continued

History of pungency selection of line WYL 77-5128B
Mean PAD

| Source Bulb Harvest | Year 8 Bulb Harvest | Year 9 Bulb Harvest | Year 10 Bulb Harvest | Year 11 Bulb Harvest |
|---|---|---|---|---|
| RNR 5621-8 (selection of 00335-1) | | | 4.67 g FW (1) 6.01 g FW (2) | |
| RNR 5621-10 (selection of 00335-1) | | | 4.87 g FW (1) 5.75 g FW (2) | |
| RNR 5621-12 (selection of 00335-1) | | | 4.81 g FW (1) 6.00 g FW (2) | |
| RNR 5621-13 (selection of 00335-1) | | | 4.29 g FW (1) 5.99 g FW (2) | |
| RNR5621-15 (selection of 00335-1) | | | 4.37 g FW (1) 5.90 g FW (2) | |
| Vidalia Sweets (SD) | | 9.15 g FW (4) | 3.34 g FW (4) | 3.20 g FW (4) |
| Vision (long day Spanish Variety) | | 9.15 g FW (3) | 6.16 g FW (1) 8.71 g FW (2) | 5.50 g FW (1) 7.35 g FW (2) |
| TX 1015Y (SD control variety) | | | 4.69 g FW (4) | 4.69 g FW (4) |
| Peruvian Sweet (SD) | | | 6.02 g FW (4) | 4.30 g FW (4) |

(1) After two months storage
(2) After six months storage
(3) Field received damage from a hail storm prior to harvest, which reduced size and stopped normal maturity and made much smaller bulbs.
(4) Locally purchased source Example 4

Long Day Length Types Storage Onions

Long day length type, low pungency onions were stored under storage conditions of 5 degrees centigrade and 50% relative humidity for 6 months and evaluated far marketable yield. Marketable yield, sometimes called "storability", refers to the retention of onion quality at a high level. Quality is assessed by monitoring internal sprout development, as well as the presence of surface mold and decay.

Table 3 provides data for storability, as percentage marketable bulbs remaining after six months storage under long term storage conditions. The B line designation refers to a more advanced line, having completed several generations of selection.

TABLE 3

Storage Characteristics of WYL 77-5128B and WYL 77-5168B
% marketable bulbs

| | Storage % after 2 months | Storage % after 3 months | Storage % after 4 months | Storage % after 5 months | Storage % after 6 months |
|---|---|---|---|---|---|
| WYL 77-5128B (long day type) | 98.8% | 97.6% | 96.4% | 96.4% | 95.2% |
| WYL 77-5168B (long day type) | 98.7% | 97.4% | 97.4% | 82% | 74.3% |
| Vision (long day type) | 100.0% | 98.6% | 93.1% | 93.1% | 87.7% |
| Peruvian Sweets (SD type) | 79.7% | 72.4% | 53.6% | 37.7% | 11.6% |

The results in Table 3 demonstrate that the long day, low pungency onions provide excellent storage up to 6 months.

Example 5

WYL 77-5126B. Long, Day Onion

WYL 77-5126B, a long day onion inbred, was developed by selfing and mass selection from a synthetic gene pool of Yellow Sweet Spanish onion (synthetic gene pool YSS-7171-5B).

In Year 1, seed was produced on a single bulb (self) of synthetic YSS7171-5B seed cage lot 95-183 selfing cage.

In year 2 bulbs were grown from the year 1 self in row Yr2-7156.

In year 3, seed was grown on a mass selection of bulbs from bulb row Yr2-7156 in cage 97-311-1.

In year 4, bulbs were grown from seed source 97-311-1 in bulb row 99-7102.

In year 5, seed was grown from bulb row 99-7102 in cage 00611-1C

In year 6, bulbs were grown in bulb row 01OS3170 from cage 00611-1C. Bulbs were found to be uniform and parent breeding line WYL 77-5126B was assigned. Pungency testing on these bulbs showed line WYL 77-5126B having a pungency level of 5.82 PAD after six months storage.

In year 10, bulbs were grown in bulb row 05OS3118 from seed source 00611-1C. Pungency testing two months after storage showed line WYL 77-5126B have a pungency level of 6.3 PAD. After six months storage, WYL 77-5126B had a 5.62 PAD.

In year 11, seed was grown from bulb row 05OS3118 in cage RND1687. A mass selection of WYL77-5126B with a 3.67 PAD was made.

Example 6

WYL 77-5391B. Long, Day Onion

WYL 77-5391B, a long day onion inbred, was developed by half-sib selection and mass selection from a Yellow Sweet Spanish onion parent (WYL77-5168B).

In Year 1, bulbs were grown of source parent WYL77-5168B in bulb row 02OS3097.

In Year 2, a mass selection of WYL 77-5168B was made in cage RNR5616. A single plant of this mass selection was designated RNR5616-2 and seed from this plant was harvested as a single plant (a half-sib selection).

In Year 4, bulbs were grown in bulb row 05OS7001 from seed source RNR5616-2. Bulbs were found to be uniform and parent line WYL 77-5391B was assigned. Pungency testing two months after storage showed line WYL 77-5391B have a pungency level of 4.4 PAD. After six months storage, WYL 77-5391B had a 3.99 PAD.

In Year 6 seed was grown from bulb row 05OS7001 in cage RND1698. A mass selection of WYL77-5391B with a 3.17 PAD was made.

Example 7

WYL 77-5392B. Long, Day Onion

WYL 77-5392B, a long day onion inbred, was developed by mass selection from a Yellow Sweet Spanish onion parent (WYL77-5168B).

In Year 1, bulbs were grown of source parent WYL77-5168B in bulb row 05OS3152. Pungency testing of line WYL77-5168B after two months storage had a 4.7 PAD.

In Year 2 mass selection of WYL 77-5168B was made in cage RND1699. After six months storage this mass selection was found to have a 3.34 PAD. This mass selection was designated WYL 77-5392B, having a significant lower PAD than the original parent source.

Example 8

Plant Breeding and Line Development

Various *Allium cepa* lines of this invention can be used to transmit the long day photoperiodic response, low pungency trait to new varieties using various cross pollination and selection methods. Therefore, breeders may obtain hybrids using the described low pungency, long day onion plants and lines for further selfing and subsequent selection. Using standard crossing, backcrossing and selection techniques, those of skill in the art may obtain commercial low pungency, long day onions with various desirable traits besides those described above. For example, breeders may easily obtain commercial *Allium cepa* lines with the preferred trait of long day onion color, disease resistance traits, traits relating to optimized yield under specific growth conditions Example 9

Onion Production

Onions are usually planted in multiple rows on beds. Beds are commonly formed at or just before planting with 2 to 12 rows planted per bed. A typical arrangement is two double rows spaced about 12 inches apart on 34- or 44-inch beds. Multiple such arrangements are sometimes used, particularly with drip irrigation systems. Some low pungency onions are planted in single TOWS.

Onion seed is expensive, and is generally direct seeded with precision planters (onions are not thinned). Seed is commonly planted about ¼- to ½-inch deep. With furrow irrigation in lighter textured soils or with limited soil moisture, a depth of ¾ inch may be required.

Hybrid seed of low pungency, LD onions are planted in the conventional way and onions are grown to maturity, harvested, and maintained under long-term storage conditions for a period of two to six months. Low pungency onions are thereafter removed from storage and provided during the winter to the consumer as a sweet onion.

Although the foregoing invention has been described in some detail by way of illustration and example for purposes of clarity and understanding, it will be obvious that certain changes and modifications may be practiced within the scope of the invention, as limited only by the scope of the appended claims. All references cited herein are hereby expressly incorporated herein by reference.

Deposit Information

A deposit has been made of the *Seminis* Vegetable Seeds proprietary inbred *Allium cepa* lines disclosed above and recited in the appended claims, with NCIMB Ltd, 23 St. Machar Drive, Aberdeen AB24 3RY, an International Depositary Authority (IDA) as established under the Budapest Treaty on the International Recognition of the Deposit of Micro-organisms for the Purposes of Patent Procedure. The NCIMB accession numbers for lines WYL 77-5128B and WYL 77-5168B are, respectively, NCIMB 41329 and NCIMB 41330. The date of each of the deposits was 24 Jun. 2005.

What is claimed is:

1. An onion plant, or a part thereof, said onion plant grown from a seed obtained by crossing a first onion plant and a second onion plant, said first onion plant is of a variety selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait.

2. The onion plant, or a part thereof, of claim 1, wherein said second onion plant is selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and a line of WYL 77-5168B which possesses a male sterility trait.

3. The onion plant, or a part thereof, of claim 1, wherein said onion plant is a Spanish onion type.

4. The onion plant, or a part thereof, of claim 1, wherein the pungency of a bulb produced by said onion plant is low pungency measured by an average PAD measurement less than 5.0 μmol/g FW pyruvate at harvest.

5. The onion plant, or a part thereof, of claim 1, wherein said onion plant grown from said seed produces a bulb that maintains low pungency after storage for a period of about 4 months.

6. The onion plant, or a part thereof, of claim 1, wherein said onion plant grown from said seed is further characterized as producing a bulb which has an average PAD value that increases no more than 10% after storage for two months at 5 degrees centigrade and 50% relative humidity.

7. A method of producing a hybrid onion seed; said method comprising:
crossing a first onion plant of a variety selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait with a second onion plant; and
obtaining $F_1$ onion seed.

8. The method of claim 7, wherein said second onion plant is a plant of a variety selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait.

9. An onion seed produced by the method of claim 7.

10. A method of producing an onion plant, or a part thereof, of an $F_1$ hybrid plant requiring 14 or more contiguous hours of daylight to initiate bulb formation and having low pungency comprising:
crossing a first low pungency onion plant requiring 14 or more hours of daylight to initiate bulb formation with a second onion plant;
obtaining an $F_1$ onion seed requiring 14 or more contiguous hours of daylight to initiate bulb formation and having low pungency; and
growing said $F_1$ onion seed;
wherein said $F_1$ hybrid plant is characterized as producing bulbs having low pungency that is measured by an average pyruvic acid development (PAD) value of less than 5.5 micromoles (μmol) pyruvic acid/gram fresh weight (μmol/g FW pyruvate) at harvest, wherein said $F_1$ hybrid plant is further characterized as producing bulbs which have an average PAD value that increases no more than 20% after storage for two months at 5 degrees centigrade and 50% relative humidity, and wherein said first low pungency onion plant is of a variety selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait.

11. The method of claim 10, wherein said low pungency is measured by an average PAD measurement less than 5.0 μmol/g FW pyruvate at harvest.

12. The method of claim 10, wherein said $F_1$ hybrid plant is further characterized as producing bulbs that maintain low pungency after storage for a period of about 4 months.

13. The method of claim 10, wherein said $F_1$ hybrid plant is further characterized as producing bulbs which have an average PAD value that increases no more than 10% after storage for two months at 5 degrees centigrade and 50% relative humidity.

14. The method of claim 10, wherein said second onion plant is selected from the group consisting of WYL 77-5128B having seed deposited as NCIMB Accession No. 41329, WYL 77-5168B having seed deposited as NCIMB Accession No. 41330, a WYL 77-5128B which possesses a male sterility trait, and WYL 77-5168B which possesses a male sterility trait.

15. The method of claim 10, wherein said $F_1$ hybrid plant is cytoplasmically male sterile.

16. The method of claim 10, wherein said part thereof is selected from the group consisting of a seed, a bulb, a leaf, pollen, a protoplast, an ovule and a cell.

17. A method of growing an onion plant, said method comprising:
providing an onion seed of a variety or its $F_1$ progeny, wherein said variety is characterized as producing low pungency onion plants requiring 14 or more hours of daylight to initiate bulb formation, wherein said low pungency is measured by an average pyruvic acid development (PAD) value of less than 5.5 micromoles (μmol) pyruvic acid/gram fresh weight (μmol/g FW pyruvate) at harvest, wherein said variety is further characterized as producing bulbs which have an average PAD value that increases no more than 20% after storage for two months at 5 degrees centigrade and 50% relative humidity wherein said variety is selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait; and
growing said onion seed to produce a bulb.

18. The method of claim 17, further comprising harvesting said bulb.

19. The method of claim 17, wherein said low pungency is measured by an average PAD measurement less than 5.0 μmol/g FW pyruvate at harvest.

20. The method of claim 17, wherein said variety is further characterized as producing bulbs which maintain low pungency after storage for a period of about 4 months.

21. The method of claim 17, wherein said variety is further characterized as producing bulbs which have an average PAD value that increases no more than 10% after storage at 5 degrees centigrade and 50% relative humidity for two months.

22. The method of claim 17, wherein said onion plant is cytoplasmically male sterile.

23. The onion plant, or a part thereof, of claim 4, wherein said low pungency is measured by an average Pyruvic Acid Development (PAD) measurement less than 4.5 FW pyruvate at harvest.

24. The onion plant, or a part thereof, of claim 4, wherein said low pungency is measured by an average Pyruvic Acid Development (PAD) measurement less than 4.0 µmol/g FW pyruvate at harvest.

25. The onion plant, or a part thereof, of claim 4, wherein said low pungency is measured by an average Pyruvic Acid Development (PAD) measurement less than 3.75 FW pyruvate at harvest.

26. The onion plant, or a part thereof, of claim 5, wherein said onion plant produces bulbs which maintain low pungency after storage for a period of about 6 months.

27. The method of claim 10, wherein said low pungency is measured by an average PAD measurement less than 4.5 FW pyruvate at harvest.

28. The method of claim 10, wherein said low pungency is measured by an average PAD measurement less than 4.0 µmol/g FW pyruvate at harvest.

29. The method of claim 10, wherein said low pungency is measured by an average PAD measurement less than 3.75 µmol/g FW pyruvate at harvest.

30. The method of claim 10, wherein said $F_1$ hybrid plant is further characterized as producing bulbs that maintain low pungency after storage for a period of about 6 months.

31. The method of claim 17, wherein said low pungency is measured by an average PAD measurement less than 4.5 µmol/g FW pyruvate at harvest.

32. The method of claim 17, wherein said low pungency is measured by an average PAD measurement less than 4.0 µmol/g FW pyruvate at harvest.

33. The method of claim 17, wherein said low pungency is measured by an average PAD measurement less than 3.75 µmol/g FW pyruvate at harvest.

34. The method of claim 17, wherein said $F_1$ progeny plant is further characterized as producing bulbs that maintain low pungency after storage for a period of about 6 months.

35. A population of onion plants, or onion parts thereof, each plant of said population is a long day type obtainable by crossing a first onion plant and a second onion plant, said first onion plant is of a variety selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait,
wherein said population of onion plants is characterized as producing bulbs having low pungency measured by an average pyruvic acid development (PAD) value at harvest equal to or less than the average PAD value of onion variety WYL 77-5168B or WYL 77-5128B, when grown in the same field and season, and
wherein said population of onion plants is further characterized as producing bulbs which have an average PAD value that increases no more than 20% after storage for two months at 5 degrees centigrade and 50% relative humidity.

36. A population of onion plants, or onion parts thereof, each plant of said population is of a long day type obtainable by crossing a first onion plant and a second onion plant,
said first onion plant is of a variety selected from the group consisting of WYL 77-5128B having seed deposited as NCIMB Accession No. 41329, WYL 77-5168B having seed deposited as NCIMB Accession No. 41330, WYL 77-5128B which possesses a male sterility trait, and WYL 77-5168B which possesses a male sterility trait,
wherein said population of onion plants is characterized as producing bulbs having low pungency measured by a reduction of at least 10% in one or more organosulfur compounds compared to onion line Vision grown in the same field and season, and
wherein said population of onion plants is further characterized as producing bulbs which have an average PAD value that increases no more than 20% after storage for two months at 5 degrees centigrade and 50% relative humidity.

37. The population of onion plants, or onion parts thereof, of claim 36, wherein said population of onion plants is characterized as producing bulbs having low pungency measured by a reduction of at least 15% in one or more organosulfur compounds compared to onion line Vision grown under comparable field conditions.

38. The population of onion plants, or onion parts thereof, of claim 37, wherein said population of onion plants is characterized as producing bulbs having low pungency measured by a reduction of at least 20% in one or more organosulfur compounds compared to onion line Vision grown under comparable field conditions.

39. The population of onion plants, or onion parts thereof, of claim 38, wherein said population of onion plants is characterized as producing bulbs having low pungency measured by a reduction of at least 25% in one or more organosulfur compounds compared to onion line Vision grown under comparable field conditions.

40. The population of onion plants, or onion parts thereof, of claim 39, wherein said population of onion plants is characterized as producing bulbs having low pungency measured by a reduction of at least 30% in one or more organosulfur compounds compared to onion line Vision grown under comparable field conditions.

41. The population of onion plants, or onion parts thereof, of claim 40, wherein said population of onion plants is characterized as producing bulbs having low pungency measured by a reduction of at least 35% in one or more organosulfur compounds compared to onion line Vision grown under comparable field conditions.

42. The population of onion plants, or onion parts thereof, of claim 36, wherein said one or more organosulfur compounds are selected from the group consisting of 1-propenyl cysteine sulfoxide, methyl-cysteine sulfoxide, and propyl cysteine sulfoxide.

43. The population of onion plants, or onion parts thereof, of claim 36, wherein said onion parts are selected from the group consisting of seeds, leaves, pollens, cotyledons, hypocotyls, embryos, roots, pods, flowers, shoots, bulbs, and stems.

44. The onion plant, or a part thereof, of claim 1, wherein said onion plant is a male sterile Spanish onion type.

45. The onion plant, or a part thereof, of claim 1, wherein said onion part is selected from the group consisting of seed, leaf, pollen, cotyledon, hypocotyl, embryo, root, pod, flower, shoot, bulb, and stem.

* * * * *